(12) United States Patent
Nakanishi et al.

(10) Patent No.: US 7,825,286 B2
(45) Date of Patent: Nov. 2, 2010

(54) 6,8,10-UNDECATRIEN-3-OL OR 6,8,10-UNDECATRIEN-4-OL, AND AROMA COMPOSITIONS

(75) Inventors: Akira Nakanishi, Tokyo (JP); Yasutaka Ohkubo, Yokohama (JP); Naomi Tomita, Kawasaki (JP); Tomoko Maeda, Tokyo (JP); Norio Miyazawa, Tokyo (JP)

(73) Assignee: T. Hasegawa Co., Ltd., Tokyo (JP)

( * ) Notice: Subject to any disclaimer, the term of this patent is extended or adjusted under 35 U.S.C. 154(b) by 0 days.

(21) Appl. No.: 12/452,081

(22) PCT Filed: Jun. 6, 2008

(86) PCT No.: PCT/JP2008/060809

§ 371 (c)(1),
(2), (4) Date: Dec. 15, 2009

(87) PCT Pub. No.: WO2008/153112

PCT Pub. Date: Dec. 18, 2008

(65) Prior Publication Data

US 2010/0130794 A1    May 27, 2010

(30) Foreign Application Priority Data

Jun. 15, 2007 (JP) .............................. 2007-158946
Mar. 3, 2008  (JP) .............................. 2008-051939

(51) Int. Cl.
C07C 33/02    (2006.01)
C07C 29/143   (2006.01)
A61K 8/18     (2006.01)

(52) U.S. Cl. .................... 568/880; 568/902; 568/909.5; 512/25

(58) Field of Classification Search ................. 568/880, 568/802, 909.5
See application file for complete search history.

(56) References Cited

U.S. PATENT DOCUMENTS

| 3,960,977 A | 6/1976 | Naf et al. |
| 4,014,951 A | 3/1977 | Naf et al. |
| 2004/0242453 A1 | 12/2004 | Decorzant et al. |

FOREIGN PATENT DOCUMENTS

| EP | 0 100 015 | 5/1985 |
| JP | 50-32105 | 3/1975 |
| JP | 59-42326 | 3/1984 |
| JP | 61-111666 | 5/1986 |
| JP | 61-172839 | 10/1986 |
| JP | 2005-515249 | 5/2005 |
| JP | 4057638 | 3/2008 |
| JP | 4057639 | 3/2008 |

OTHER PUBLICATIONS

Berger et al., "Novel Volatiles in Pineapple Fruit and Their Sensory Properties", J. Agric. Food Chem., vol. 33, 1985, pp. 232-235.
Berger et al., "Natural Occurrence of Undecaenes in Some Fruits and Vegetables", Journal of Food Science, vol. 50, 1985, pp. 1655-1656.
International Search Report issued Aug. 12, 2008 in International (PCT) Application No. PCT/JP2008/060809.

*Primary Examiner*—Sikarl A Witherspoon
(74) *Attorney, Agent, or Firm*—Wenderoth, Lind & Ponack, L.L.P.

(57) ABSTRACT

This invention offers 6,8,10-undecatrien-3-ol and 6,8,10-undecatrien-4-ol. These compounds possess not only woody green note, but also fruity note rich in naturality and freshness, and aroma compositions blended therewith are useful for imparting fragrance and flavor to food and beverage, perfumed cosmetics, medicaments and the like.

5 Claims, No Drawings

6,8,10-UNDECATRIEN-3-OL OR 6,8,10-UNDECATRIEN-4-OL, AND AROMA COMPOSITIONS

TECHNICAL FIELD

This invention relates to 6,8,10-undecatrien-3-ol or 6,8,10-undecatrien-4-ol which are useful as aroma compounds, and to aroma compositions which contain these compounds as the active ingredient.

BACKGROUND ART

It is known that polyunsaturated compounds possess significant aroma characteristics. For example, JP 50 (1975)-32105A discloses presence of (3E,5E)-1,3,5-undecatriene and (3E,5Z)-1,3,5-undecatriene in galbanum essential oil, and that these compounds were synthesized and identified. Also JP 59 (1984)-42326A discloses utility of 1,3,5,7-undecatetraene as an aroma compound. Furthermore, J. Agric. Food Chem., 33 (1985), 232 and J. Food Sci., 50 (1985), 1655 report existence of (3E,5Z,8Z)-1,3,5,8-undecatetraene in pineapple, peach, mango and kiwi fruit. JP 2005-515249T discloses utility of acetal of 2,4,7-decatrienal as an aroma compound.

These polyunsaturated compounds have excellent odor. For example, JP 50 (1975)-32105A discloses that 1,3,5-undecatriene has floral note reminiscent of hyacinth, violet, narcissus, lavender or gardenia and its leafy bottom note expresses or enhances its property resembling that of the natural aroma. JP 59 (1984)-42326A discloses 1,3,5,7-undecatetraene has an earthy and woody note. JP 2005-515249T also states acetal of 2,4,7-decatrienal has pleasant natural green note.

The aroma characteristics of above-named compounds, however, are entirely different from an odor rich in naturality which is emphasized by fresh fruity note.

DISCLOSURE OF THE INVENTION

In recent years, consumers' tastes are diversified, and materials rich in naturality and freshness are in demand, as aromas for food and beverage, perfumed cosmetics and the like. At the present time, however, such demands cannot be fully met by simply combining conventional aroma substances.

Accordingly, therefore, the object of the present invention is to offer novel aroma compounds which can reproduce odor rich in naturality and freshness, and methods of their preparation.

We synthesized various derivatives of polyunsaturated compounds and investigated their aroma characteristics, noting that aforesaid polyunsaturated compounds possess excellent aroma characteristics. We now unexpectedly discovered in the course of the investigations that 6,8,10-undecatrien-3-ol or 6,8,10-undecatrien-4-ol have superb aroma characteristics and, surprisingly, their aroma not only has a woody green note but also a natural, fresh fruity note. The present invention is whereupon completed.

Thus, the present invention offers 6,8,10-undecatrien-3-ol or 6,8,10-undecatrien-4-ol, which are novel compounds never before disclosed in literature and are represented by the following formula

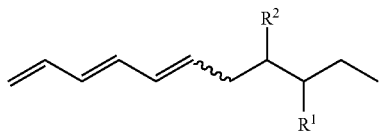

[in the formula, either one of $R^1$ and $R^2$ stands for hydrogen, and the other stands for hydroxy, the wavy line signifying cis-form, trans-form or a mixture of cis- and trans-forms at an optional ratio].

This invention also offers aroma compositions which are characterized by containing 6,8,10-undecatrien-3- or -4-ol of the formula (1) as the active ingredient.

This invention furthermore offers a method of producing 6,8,10-undecatrien-3-ol of the following formula (5)

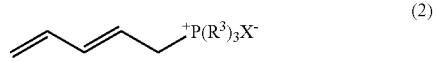

[in the formula, the wavy line signifies cis-form, trans-form or a mixture of cis- and trans-forms at an optional ratio]

which is characterized by subjecting a phosphonium salt represented by the following formula (2)

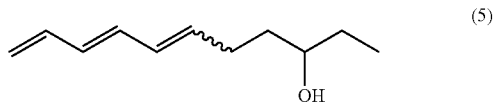

[in the formula, $R^3$ stands for an aryl and X stands for a halogen]

or a phosphonate of the following formula (3)

[in the formula, $R^4$ stands for a $C_{1-8}$ alkyl or aryl]

to Wittig reaction or Horner-Emmons reaction, with a lactol of the following formula (4)

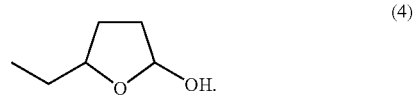

This invention also offers a method for producing 6,8,10-undecatrien-4-ol of the following formula (7)

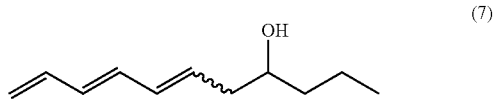

[in the formula, the wavy line signifies cis-form, trans-form, or a mixture of cis- and trans-forms at an optional ratio]

which is characterized by reducing 6,8,10-undecatrien-4-one represented by the following formula (6)

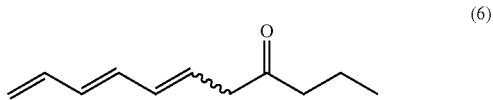

(6)

[in the formula, the wavy line signifies cis-form, trans-form, or a mixture of cis- and trans-forms at an optional ratio].

The compounds of the formula (1) according to the present invention have, in addition to woody green note, natural, fresh and fruity note with excellent lasting effect, and are useful as constituent materials of aroma compositions for food and beverage, perfumed cosmetics; health and sanitation goods and medicaments.

Hereinafter the compounds of the invention, methods of their preparation and their utility for aroma compositions are explained in further details.

6,8,10-Undecatrien-3-ol of the formula (5) which is included among the compounds of the formula (1) of this invention (a compound of the formula (1), in which $R^1$=OH and $R^2$=H) can be synthesized, for example, according to the following reaction scheme 1.

Reaction Scheme 1

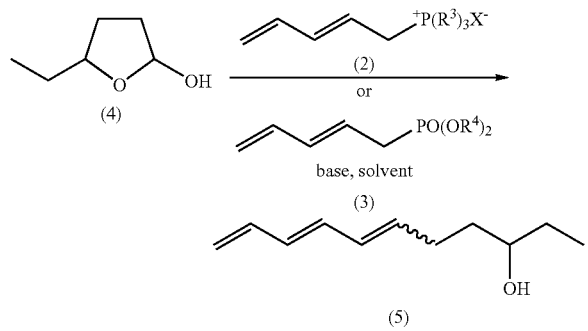

[in the formula, the wavy line signifies cis-form, trans-form or a mixture of cis- and trans-forms at an optional ratio, $R^3$ stands for an aryl, X stands for a halogen, and $R^4$ stands for a $C_{1-8}$ alkyl or aryl].

In the present specification, "aryl" is a monocyclic or polycyclic aromatic hydrocarbon group, for example, an optionally substituted phenyl, tolyl, naphthyl or the like, preferably phenyl.

"Alkyl" is a straight chain or branched chain saturated hydrocarbon group, for example, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, 1,1-dimethylpropyl, 1,2-dimethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl or the like. Of those, $C_{1-4}$ alkyl groups are preferred.

As particularly preferred halogens represented by X, Cl and Br can be named.

The Wittig reaction of a phosphonium salt of the formula (2) with a lactol of the formula (4), or the Horner-Emmons reaction of a phosphonate of the formula (3) with a lactol of the formula (4) can be performed under the typical conditions for these reactions as described in the literature (e.g., see Shin-jikkenkagaku Koza (lectures on new experimental chemistry) 14, Syntheses and reactions of organic compounds [1], p. 224-243).

The Wittig reaction of a phosphonium salt of the formula (2) with a lactol of the formula (4) can be performed in an inert organic solvent in the presence of a base. Examples of the organic solvent include ether (e.g., diethyl ether, diisopropyl ether, methyl t-butyl ether, 1,4-dioxane, tetrahydrofuran and the like); halogenated hydrocarbon (e.g., dichloromethane, chloroform and the like); aromatic hydrocarbon (e.g., benzene, toluene, xylene and the like); and polar solvent (e.g., dimethylformamide, dimethylsulfoxide, acetonitrile and the like). In particular, toluene, tetrahydrofuran, dimethylsulfoxide, dimethylformamide or mixture thereof are preferred.

As the base, any of the bases usually used in Wittig reaction can be used, examples of which include alkali metal hydroxide (e.g., sodium hydroxide, potassium hydroxide, lithium hydroxide and the like); alkali metal hydride (e.g., sodium hydride, potassium hydride and the like); organolithium compound (e.g., n-butyllithium, t-butyllithium, phenyllithium and the like); alkali metal amide (e.g., lithium amide, potassium amide, sodium amide, lithium diisopropyl amide and the like); alkali metal hexamethyldisilazide; and alkali metal alcoholate (e.g., sodium methoxide, sodium ethoxide and the like). The use rate of these bases is normally within a range of 0.8-5 equivalent, preferably 1-3 equivalent, to the phosphonium salt of the formula (2).

Also the use rate of the lactol of the formula (4) to the phosphonium salt of the formula (2) is within a range of normally 0.8-5 equivalent, preferably 1-3 equivalent.

The Wittig reaction can be performed normally at temperatures within a range of −78 to 60° C., preferably from −10 to 25° C., normally for about 0.5-24 hours, preferably about 0.5-2 hours.

The Horner-Emmons reaction of a phosphonate of the formula (3) with a lactol of the formula (4) can be performed in the manner similar to the Wittig reaction of a phosphonium salt of the formula (2) with a lactol of the formula (4).

Thus, depending on the reaction conditions adopted, 6,8,10-undecatrien-3-ol of the formula (5) in which the cis-form: trans-form ratio at the wavy line in the formula (5) lies within a range of generally 10:1-1:10, preferably 7:3-3:7, is obtained in the form of a mixture of geometrical isomers.

Method of preparing the lactol of the formula (4) to be used as a starting material is not critical. For example, it can be synthesized according to the following reaction scheme 2.

Reaction Scheme 2

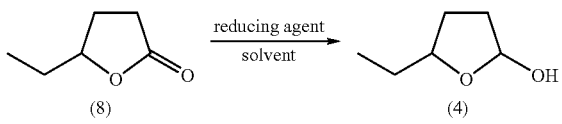

Synthesis of Lactol of the Formula (4)

Lactol of the formula (4) can be obtained by reacting γ-hexylactone of the formula (8) with a reducing agent such as, for example, diisobutylaluminum hydride (DIBAL), dimethoxyethoxy-sodium aluminum hydride, sodium borohydride, lithium aluminum hydride and the like, in an inert gaseous atmosphere, in an inert organic solvent such as toluene, hexane, dichloromethane, tetrahydrofuran and the like, at temperatures ranging from −78 to 20° C., for around 1-10 hours. The γ-hexylactone of the formula (8) which is the starting material is marketed and readily available.

The phosphonium salt of the formula (2) or the phosphonate of the formula (3) are known compounds which can be synthesized following the method disclosed in JP 50 (1975)-32105A. As an example, the following reaction scheme 3 may be cited.

Reaction Scheme 3

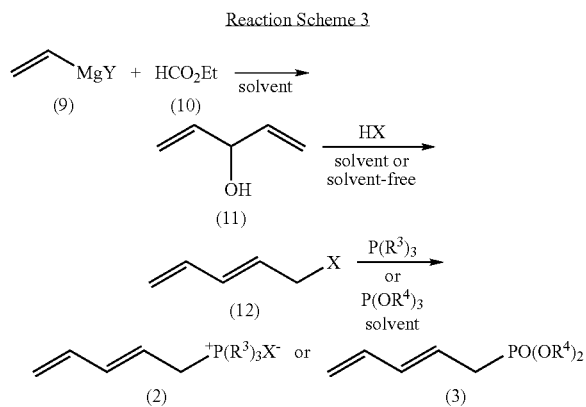

[in the formulae, $R^3$ stands for an aryl, X stands for a halogen, and $R^4$ stands for a $C_{1-8}$ alkyl or aryl].

Synthesis of a Phosphonium Salt of the Formula (2) or a Phosphonate of the Formula (3)

A Grignard reagent of the formula (9) which is the starting material can be readily prepared by treating vinyl halide with magnesium metal in an organic solvent. As the vinyl halide, for example, vinyl chloride, vinyl bromide, vinyl iodide and the like can be used, vinyl chloride and vinyl bromide being particularly preferred. As the solvent useful in this reaction, those generally used in Grignard reaction can be similarly used, examples of which include diethyl ether, dipropyl ether, dimethoxyethane, tetrahydrofuran, dioxane and the like, among which diethyl ether and tetrahydrofuran are particularly preferred. The use rate of the Grignard reagent of the formula (9) is not particularly limited, so long as it is at least 2 mol per mol of ethyl formate of the formula (10), while in consideration of economy, it is preferably within a range of 2-2.2 mol.

The reaction of Grignard reagent of the formula (9) with ethyl formate of the formula (10) can be performed normally at temperatures within a range of −10 to 40° C., preferably 0 to 15° C. Purifying the product after completion of the reaction by the means customarily practiced, such as extraction, washing, drying, concentration and if necessary distillation, the alcohol of the formula (11) can be obtained.

In the above Grignard reaction, the alcohol of the formula (11) can be similarly obtained when acrolein is used in place of ethyl formate.

Then subjecting the alcohol of the formula (11) to a nucleophilic substitution reaction with hydrogen halide (HX), the halide of the formula (12) is obtained. This reaction can be performed by adding a 20-40% aqueous solution of hydrogen halide to the alcohol of the formula (11), in the presence of such a solvent as diethyl ether, tetrahydrofuran or the like, or in the absence of solvent. As the useful hydrogen halide (HX), for example, hydrogen chloride, hydrogen bromide, hydrogen iodide and the like can be named, which is added in an amount ranging 1-2 mol per mol of the alcohol of the formula (11). The time for addition is normally 0.5-3 hours, preferably 1-2 hours, and suitable reaction temperature is within a range of normally −10 to 40° C., preferably 0 to 15° C. After completion of the reaction, the halide of the formula (12) can be obtained by purifying the product by a conventional method such as extraction, washing, drying, concentration and, where necessary, distillation.

Successively the halide of the formula (12) is reacted with phosphine $[P(R^1)_3]$ or phosphite $[P(OR^2)_3]$ according to a conventional method to produce the phosphonium salt of the formula (2) or phosphonate of the formula (3). This reaction can be performed either in the presence or absence of a solvent, examples of useful solvent including methanol, ethanol, propanol, isopropanol, butanol, chloroform, dichloromethane, 1,2-dichloroethane, tetrahydrofuran, dimethyl ether, dimethylformamide, dimethylsulfoxide, toluene and the like. These solvents can be used each by itself or in combination of two or more. The use rate of such a solvent is subject to no particular limitation. For example, it can be used in an amount of around 1-50 weight times preferably around 2-10 weight times, that of the halide of the formula (12). The above reaction can be performed generally at the temperatures within a range of about −20 to 100° C., for around 1-72 hours, whereby the phosphonium salt of the formula (2) or phosphonate of the formula (3) can be obtained. The resulting phosphonium salt of the formula (2) or phosphonate of formula (3) can be easily isolated by such means as crystallization, or the like.

6,8,10-Undecatrien-4-ol of the formula (7) which is included among the compounds of the formula (1) of this invention (a compound of the formula (1) in which $R^1$=H and $R^2$=OH) can be synthesized, for example, according to the following reaction scheme 4.

Reaction Scheme 4

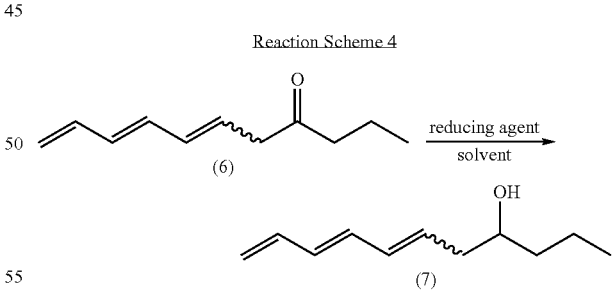

[in the formula, the wavy line signifies cis-form, trans-form or a mixture of cis- and trans-forms at an optional ratio].

The reduction of 6,8,10-undecatrien-4-one of the formula (6) can be performed under the conditions typical for the reaction to reduce ketone to alcohol. More specifically, for example, reductions described in literature (see "Shin-jikken-kagaku Koza" 15, Oxidation and Reduction [II]) using diisobutylaluminum hydride, lithium aluminum hydride or sodium borohydride, or by Meerwein-Ponndorf-Verley reduction, can be performed. In particular, reduction with diisobutylaluminum hydride, lithium aluminum hydride, or sodium borohydride is preferred.

Thus, depending on the starting material and/or the reaction conditions adopted, 6,8,10-undecatrien-4-ol of the formula (7) in which the cis:trans ratio at the wavy line in the formula (7) lies within a range of generally 10:1-1:10, preferably 7.3-3:7, is obtained in the form of a mixture of geometrical isomers.

6,8,10-Undecatrien-4-one of the formula (6) can be used as the starting material irrelevantly to its preparation method. For example, it can be synthesized according to the following reaction scheme 5.

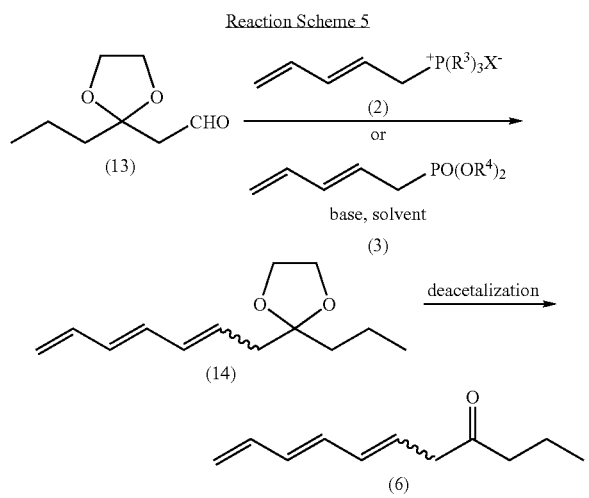

[in the formulae, the wavy line signifies cis-form, trans-form, or a mixture of cis- and trans-forms at an optional ratio; $R^3$ stands for an aryl; X stands for a halogen atom; and $R^4$ stands for a $C_{1-8}$ alkyl or aryl].

The Wittig reaction of a phosphonium salt of the formula (2) with an aldehyde of the formula (13) or the Horner-Emmons reaction of a phosphonate of the formula (3) with an aldehyde of the formula (13) can be performed in the manner similar to the Wittig reaction of a phosphonium salt of the formula (2) with a lactol of the formula (4) as earlier described, whereby a trieneacetal of the formula (14) can be obtained in the form of a mixture of cis/trans geometrical isomers.

The reaction to produce 6,8,10-undecatrien-4-one of the formula (6) by deacetalization of the trieneacetal of the formula (14) can be performed under customarily adopted deacetalization conditions as described in literature (see, for example, Protective Groups in Organic Synthesis, Greene Wuts, p. 317-322). It can thus be performed, for example, by an acetal exchange reaction using an acid catalyst (e.g., pyridinium p-toluenesulfonate (PPTS)-acetone-water, p-toluenesulfonic acid (TsOH)-acetone, or the like); hydrolysis using an acid catalyst (e.g., hydrochloric acid-tetrahydrofuran, acetic acid, perchloric acid or the like); or oxidation (DDQ-acetonitrile-water, or the like).

As the aldehyde of the formula (13), any aldehyde can be used irrelevantly to the method of preparation thereof. It can be synthesized, for example, according to the following reaction scheme 6.

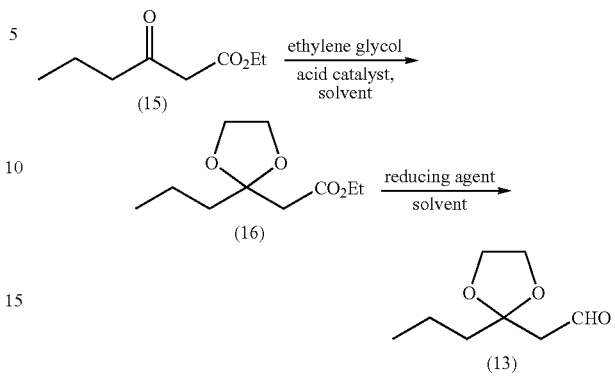

Synthesis of Aldehyde of the Formula (13)

The acetalization of ethyl 3-oxohexanoate of the formula (15) with ethylene glycol can be performed under the conditions typical for these reactions as described in literature (for example, see Protective Groups in Organic Synthesis, Greene Wuts, p. 312-316). For example, by carrying out the reaction in an azeotropic solvent of benzene, toluene, cyclohexane or the like with water, using an acid catalyst such as pyridinium p-toluenesulfonate (PPTS), p-toluenesulfonic acid (TsOH), camphorsulfonic acid (CSA) or the like, at the boiling point of the solvent while removing the formed water, the compound of the formula (16) can be produced.

Then the compound of the formula (16) is reduced in an inert gaseous atmosphere, using a reducing agent such as, for example, diisobutylaluminum hydride (DIBAL), in an inert organic solvent such as toluene, hexane or the like, to provide the aldehyde of the formula (13).

The compounds of the formula (1) offered by the present invention are capable of imparting fresh and very natural note to aroma compositions, when blended therewith at a specific ratio.

Thus, according to the invention, aroma compositions can be offered, which are characterized by containing a compound of the formula (1) as the active ingredient.

The compounds of the formula (1) to be blended with the aroma compositions have the fragrance and flavor characteristics as above, regardless of the form of bond at the part indicated with the wavy line in the formula (1), which may be cis-form, trans-form or a mixture of cis- and trans-forms at an optional ratio. Accordingly, the compounds of the invention are useful in the aroma compositions, irrelevantly to the geometrical configuration of the part indicated with the wavy line.

When a compound of the formula (1) is blended with an aroma composition, its blend ratio differs depending on the purpose of blending, kind of the aroma composition and so on. Whereas, it can normally be within a range of 0.00001-10 wt %, preferably 0.001-0.1 wt %, based on the total amount of the aroma composition.

Addition of a compound of the formula (1) at such ratios to, for example, aroma compositions of fruits (e.g., strawberry, blueberry, raspberry, apple, cherry, plum, apricot, peach, pineapple, banana, melon, mango, papaia, kiwi fruit, pear, grape, muscat, "Kyoho" grape and the like); citrus fruits (e.g., lemon, orange, grapefruit, lime, mandarin and the like); Japanese citrus flavor (e.g., "mikan; *Citrus unshiu*", "kabosu;

*Citrus sphaerocarpa*", "sudachi; *Citrus sudachi*", "hassaku; *Citrus hassaku*", "iyokan; *Citrus iyo*","yuzu; *Citrus junos*", "shekwasha; *Citrus depressa*", kumquat and the like); and tea (e.g., black tea, oolong tea, green tea and the like) can emphasize the flavor of fresh natural fruit. Also addition of a compound of the formula (1) at such ratios to perfume preparations of bergamot note, geranium note, rose note, bouquet note, hyacinth note, orchid note or floral note can enhance the characteristic fragrance of individual perfume and reproduce the fresh, natural note inherent in natural essential oil.

According to the invention, furthermore, food and beverage; perfumed cosmetics; hygienic, sanitary and medicinal products, which contain the compounds of the formula (1) as fragrance or flavor component can be offered, by blending those aroma compositions containing the compounds of the formula (1) as the active ingredient with those products.

Addition of a suitable amount of an aroma composition containing a compound of the formula (1) as the active ingredient to, for examples, beverages such as carbonated beverage, fruit juice beverage, fruit wine beverage, milk beverage, and the like; frozen deserts such as ice cream, sherbet, ice candy and the like; luxury foods such as Japanese style confection, Western style confection, chewing gum, bread, coffee, black tea, tea, tobacco and the like; soup such as Japanese style soup and Western style soup; processed meat products such as ham and sausage; seasoning, various instant foods and beverages, and various snacks, enables to offer such food and beverages imparted with the unique aroma and flavor. Also addition of a suitable amount of an aroma composition containing a compound of the formula (1) as the active ingredient to, for example, shampoo, hair cream and other base preparations for hair; face powder, lipstick and other cosmetic bases or bases for toiletry washing powder or lotion can offer cosmetics perfumed with the unique fragrance. Furthermore, by blending a suitable amount of an aroma composition containing a compound of the formula (1) as the active ingredient with, for example, washing detergent, antiseptic detergent, deodorizing detergent and other hygienic and sanitary detergent; toothpaste, tissue paper, toilet paper, and the like; various hygienic sanitary materials, medicinal products and the like which are imparted with the unique fragrance can be offered.

Hereinafter the present invention is explained more specifically, referring to Examples.

EXAMPLES

Example 1

Following the series of the reaction formulae as presented below, 6,8,10-undecatrien-3-ol of the formula (5) was synthesized. The percentages in the parentheses under the Step Nos. indicate the yield in each step.

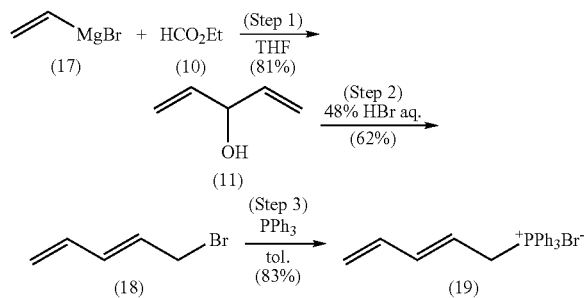

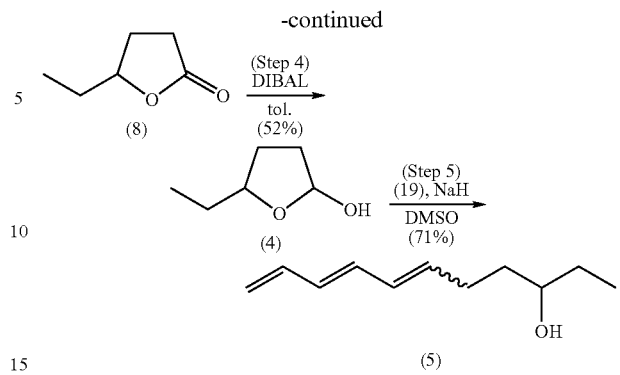

Step 1: Synthesis of the Alcohol (11)

In argon atmosphere, magnesium (48.6 g 2.00 mol), tetrahydrofuran (300 mL) and iodine (cat.) were added to a 2 L flask, and while they were stirred at room temperature, a solution (ca. 20 mL) of vinyl bromide (214.0 g, 2.00 mol) in tetrahydrofuran (780 mL) was added dropwise. The mixture was heated to 30 to 40° C. to initiate the reaction, and the remainder of vinyl bromide in tetrahydrofuran was added dropwise over 1 h, so as to maintain the reaction temperature at 30 to 40° C. After completion of the dropping, the reaction solution mixture was stirred for 1.5 h at room temperature, followed by cooling with ice-water. Then ethyl formate (10) (74.0 g, 1.00 mol) was added dropwise over 1 h at 5 to 15° C., followed by stirring for 1 h at room temperature. The reaction solution was poured into saturated aqueous ammonium chloride solution (1 L), the organic layer was separated, and the aqueous layer was extracted with diethyl ether. All of the organic layers were combined and successively washed with saturated aqueous ammonium chloride solution and saturated sodium chloride solution. Then the organic layer was dried over magnesium sulfate, and evaporated under reduced pressure. The resulting residue (96.7 g) was distilled under reduced pressure (ca. 54° C./7.8 kPa) to give the alcohol (11) (68.2 g, 0.811 mol, yield 81%, purity 96%).

Step 2: Synthesis of Bromide (18)

The alcohol (11) (52.5 g, 0.625 mol) was added to a 300 mL flask, and while they were cooled with ice-methanol, 48% aqueous hydrogen bromide solution (126.2 g, 0.749 mol) was added dropwise over 1.5 h. The organic layer was separated, and washed with water. Then the organic layer was dried over magnesium sulfate to give the bromide (18) (57.1 g, 0.388 mol, yield 62%, purity 97%).

Step 3: Synthesis of the Phosphonium Salt (19)

Triphenylphosphine (106.8 g, 0.407 mol) and toluene (250 mL) were added to a 500 mL flask and the bromide (18) (57.1 g, 0.388 mol) was added dropwise over 15 min at room temperature. After stirring for 22 h at room temperature, the precipitated crystals were separated by filtration to give the phosphonium salt (19) (132.4 g, 0.323 mol, yield 83%).

Step 4: Synthesis of the Lactol (4)

In argon atmosphere, γ-hexylactone (8) (11.4 g, 0.100 mol) and toluene (200 mL) were added to a 500 mL flask and diisobutylaluminum hydride (DIBAL) (1.01 M in toluene, 109 mL, 0.110 mol) was added dropwise over 30 min at −63 to −61° C. After completion of the dropping, the reaction mixture was stirred for 1 h at the temperature as it was, followed by addition of methanol (20 mL), Celite® and diethyl ether, and stirring overnight at room temperature. The mixture was filtered, and the filtrate was evaporated under reduced pressure. The resulting residue (13.5 g) was distilled under reduced pressure (ca. 55° C./0.5 kPa) to give the lactol (4) (6.00 g, 0.0517 mol, yield 52%, purity 93%).

Step 5: Synthesis of 6,8,10-undecatrien-3-ol (5)

In argon atmosphere, dimethylsulfoxide (DMSO) (20 mL) was added to a 100 mL flask and sodium hydride (60% oil dispersion, 1.38 g, 34.4 mmol) was added at room temperature, followed by stirring for 1 h as it was. A solution of the phosphonium salt (19) (14.1 g, 34.4 mmol) in DMSO (10 mL) was added and stirred for 10 min at room temperature, and successively a solution of the lactol (4) (2.00 g, 17.2 mmol) in DMSO (10 mL) was added at room temperature. After stirring overnight, the reaction solution was poured into water and extracted with diethyl ether. The organic layer was washed successively with water and saturated aqueous sodium chloride solution, dried over magnesium sulfate, filtered and concentrated under reduced pressure. Diethyl ether was added to the residue, and the precipitated crystals were separated by filtration. The filtrate was concentrated under reduced pressure. Once again diethyl ether was added to the residue, and the precipitated crystals were separated by filtration, and the filtrate was concentrated under reduced pressure. The resulting residue was purified by silica gel column chromatography (hexane:ethyl acetate=30:1) to give 6,8,10-undecatrien-3-ol (5) (2.04 g, 12.3 mmol, yield 71%).

Properties of 6,8,10-undecatrien-3-ol (5)

Ratio of the geometrical isomers at 6-position: E:Z=10:7

$^1$H-NMR (mixture of geometrical isomers at 6-position, CDCl$_3$, 400 MHz): δ 0.92 (3H, t, J=7.2), 1.40-1.57 (4H, m), 2.02-2.32 (2H, m), 3.52 (1H, br qui, J=3.6), 5.03, 5.07 (total 1H, each d, J=10.0, J=10.4), 5.15, 5.20 (total 1H, each d, J=16.4, J=16.8), 5.47, 5.72 (total 1H, each dt, J=7.6, 10.8, J=6.8, 15.6), 5.99-6.54 (4H, m).

$^{13}$C-NMR (mixture of geometrical isomers at 6-position, CDCl$_3$, 100 MHz): δ 9.86, 9.88, 24.2, 29.1, 30.2, 30.3, 36.3, 36.6, 72.7, 116.5, 117.1, 128.3, 128.8, 130.5, 131.3, 132.6, 133.2, 133.3, 135.2, 137.0, 137.1.

MS (m/z): 31(13), 41(34), 57(27), 67(21), 79(63), 91(100), 105(52), 119(25), 166 (M$^+$, 11)

Example 2

Following the series of the reaction formulae as presented below, 6,8,10-undecatrien-4-ol of the formula (7) was synthesized. The percentages in the parentheses under the Step Nos. indicate the yield in each step.

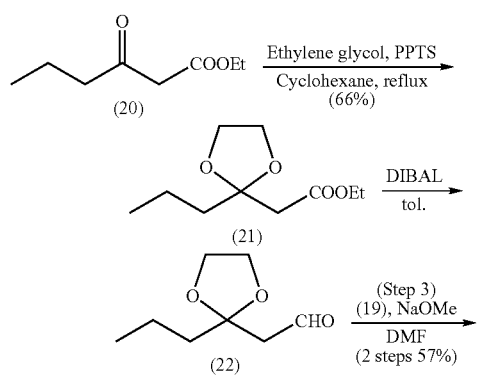

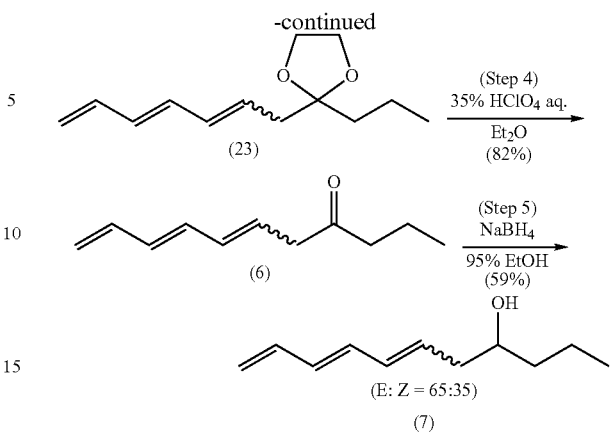

Step 1: Synthesis of the Ester (21)

Ethyl 3-oxohexanoate (12.0 g, 78.9 mmol), ethylene glycol (9.40 g, 151 mmol), pyridinium p-toluenesulfonate (PPTS) (0.1 g) and cyclohexane (50 mL) were added to a 200 mL flask, and the mixture was refluxed for 9 h while removing the generated water. Then p-toluenesulfonic acid (TsOH) (cat.) was added, followed by refluxing for 6 h, while removing the generated water. After cooling, saturated aqueous sodium hydrogencarbonate solution was added to the reaction mixture and the organic layer was separated. The organic layer was successively washed with water and saturated aqueous sodium chloride solution, dried over magnesium sulfate, and evaporated under reduced pressure. The resulting residue (14.9 g) was distilled under reduced pressure (ca. 77° C./0.2 kPa) to give the ester (21) (10.6 g, 52.4 mmol, yield 66%).

Step 2: Synthesis of the Aldehyde (22)

In argon atmosphere, the ester (21) (5.00 g, 24.7 mmol) and toluene (50 mL) were added to a 200 mL flask and diisobutylaluminum hydride (DIBAL) (0.99 M in toluene, 27.5 mL, 27.2 mmol) was added dropwise over 30 min while stirring at −65 to −60° C., followed by stirring for 30 min at the temperature as it was. The reaction mixture was poured into 5% aqueous oxalic acid dihydrate solution (140 mL), the organic layer was separated, and the aqueous layer was extracted with ethyl acetate. All of the organic layers were combined and washed with saturated aqueous sodium chloride solution. Then the organic layer was dried over magnesium sulfate, and evaporated under reduced pressure. The resulting residue (the aldehyde (22), 4.20 g) was used in the next step as it was.

Step 3: Synthesis of the Trieneacetal (23)

In nitrogen atmosphere, the aldehyde (22) (4.20 g), the phosphonium salt (19) (10.1 g, 27.2 mmol) which was obtained in a reaction similar to Example 1 and dimethylformamide (DMF) (16 g) were added to a 200 mL flask and sodium methoxide (28% in methanol, 5.00 g, 25.9 mmol) was added dropwise while cooling with ice-water, followed by stirring for 1 h at the temperature as it was. The reaction mixture was poured into saturated aqueous ammonium chloride solution, to which hexane was added, and the precipitated crystals were separated by filtration. The filtrate was extracted with hexane and washed successively with water and saturated aqueous sodium chloride solution, dried over magnesium sulfate and evaporated under reduced pressure. The resulting residue (5.92 g) was distilled under reduced pressure (ca. 100° C./0.2 kPa) to give the trieneacetal (23) (2.94 g, 14.1 mmol, yield 57%).

Step 4: Synthesis of 6,8,10-undecatrien-4-one (6)

Thirty-five (35) % aqueous perchloric acid solution (40 mL) and diethyl ether (10 mL) were added to a 200 mL flask and a solution of the trieneacetal (23) (2.94 g, 14.1 mmol) in diethyl ether (30 mL) was added dropwise over 10 min while cooling with ice-water, followed by stirring for 20 min at the temperature as it was. The reaction mixture was neutralized to pH 7-8 with saturated aqueous sodium hydrogencarbonate solution and extracted with diethyl ether. The organic layer was washed successively with water and saturated aqueous sodium chloride solution, dried over magnesium sulfate, and evaporated under reduced pressure. The resulting residue (2.61 g) was purified by silica gel column chromatography (hexane:ethyl acetate=80:1) to give 6,8,10-undecatrien-4-one (6) (1.90 g, 11.6 mmol, yield 82%).

Step 5: Synthesis of 6,8,10-undecatrien-4-ol (7)

6,8,10-Undecatrien-4-one (6) (1.50 g, 9.13 mmol) and 95% ethanol (10 mL) were added to a 50 mL flask and sodium borohydride (NaBH$_4$) (174 mg, 4.57 mmol) was added while cooling with ice-water. After 1 h, 1N hydrochloric acid (10 mL) was added gradually, followed by stirring for 30 min at room temperature. The reaction mixture was extracted with ethyl acetate, and the organic layer was washed successively with saturated aqueous sodium hydrogencarbonate solution and saturated sodium chloride solution, dried over magnesium sulfate, and evaporated under reduced pressure. The resulting residue (1.60 g) was purified by silica gel column chromatography (hexane:ethyl acetate=50:1) to give the purified product (1.1 g). The purified product (482 mg) was further distilled under reduced pressure (ca. 140° C./0.3 kPa) to give 6,8,10-undecatrien-4-ol (7) (380 mg, 2.29 mmol, yield 59%).

Properties of 6,8,10-undecatrien-4-ol (7)

Ratio of the geometrical isomers at 6-position: E:Z=65:35

$^1$H-NMR (mixture of geometrical isomers at 6-position, CDCl$_3$, 400 MHz): δ 0.916, 0.922 (total 3H, each t, J=6.8), 1.32-1.50 (5H, m), 2.15-2.38 (2H, m), 3.52 (1H, br d, J=5.6), 5.06, 5.09 (total, 1H, each d, J=10.0, J=11.6), 5.18, 5.22 (total 1H each d, J=12.4, J=12.4), 5.51, 5.71 (total 1H, each dt, J=8.0, 10.4, J=7.2, 15.2), 6.10-6.52 (4H, m)

$^{13}$C-NMR (mixture of geometrical isomers at 6-position, CDCl$_3$, 100 MHz): δ 14.1, 18.88, 18.94, 35.9, 39.0, 39.1, 41.0, 70.9, 71.0, 117.0, 117.6, 128.1, 128.3, 131.0, 131.2, 132.1, 132.9, 133.3, 134.1, 136.9, 137.0.

MS (m/z): 27(7), 31(7), 43(23), 55(55), 79(100), 94(40), 105(2), 166 (M$^+$, 7)

Example 3

Odor Evaluation

An odor evaluation test was given by well trained panelists, to 0.1% ethanol solutions of each of the 6,8,10-undecatrien-3-ol as obtained in Example 1, 6,8,10-undecatrien-4-ol as obtained in Example 2, 1,3,5-undecatriene and 1,3,5,7-undecatetraene as described in JP 50 (1975)-32105A and JP 59 (1984)-42326A, respectively. The odor evaluation was performed with 30-mL sample phials each containing the 0.1% ethanol solution of each compound, and the odor at each phial mouth and that of scent paper applied with each of the solutions were examined. Five panelists' average odor evaluations are shown in Table 1.

TABLE 1

Odor Evaluation

| Compound | Odor Evaluation |
| --- | --- |
| 6,8,10-undecatrien-3-ol | woody green note accompanied by natural and fresh fruity characteristics |
| 6,8,10-undecatrien-4-ol | fruity note rich in sweet, natural and fresh characteristics in addition to woody green note |
| 1,3,5-undecatriene | floral note including fresh leafy tone |
| 1,3,5,7-undecatetraene | woody and earthy note reminiscent of leaves and flowers |

Example 4

As a pineapple-flavored, formulated aroma composition, a basic aroma composition formed of the components as shown in the following Table 2 was prepared.

TABLE 2

A Pineapple-flavored, Basic Formulated Aroma Composition

| Blended Component | Blended Amount (g) |
| --- | --- |
| ethyl acetate | 300 |
| ethyl butyrate | 250 |
| isoamyl acetate | 100 |
| isoamyl valerate | 55 |
| isobutyric acid | 70 |
| isovaleric acid | 30 |
| allyl caproate | 35 |
| ethyl caproate | 20 |
| ethyl caprylate | 15 |
| ethyl caprate | 20 |
| isoamyl alcohol | 35 |
| diethyl malonate | 30 |
| citral | 15 |
| linalool | 5 |
| maltol | 20 |
| Total | 1000 |

Novel pineapple-flavored, formulated aroma compositions were prepared by adding 0.1 g of the 6,8,10-undecatrien-3-ol as prepared in Example 1, or 0.1 g of the 6,8,10-undecatrien-4-ol as prepared in Example 2, to 99.9 g of the above composition. Aromas of these novel pineapple-flavored compositions and that of the composition as prepared in the above to which neither of the compounds was added, were compared by ten expert panelists. The result of the sensory evaluation is shown in Table 3.

TABLE 3

| Compound Blended | Odor Evaluation |
| --- | --- |
| None | control |
| 6,8,10-undecatrien-3-ol | pineapple note with enhanced fresh fruity characteristics compared with the control |
| 6,8,10-undecatrien-4-ol | very natural pineapple note with enhanced fresh fruity characteristics compared with the control |

As above, all of the ten expert panelists evaluated both of the pineapple-flavored compositions blended with the aroma compounds as well reproducing the characteristic odor of natural pineapple and markedly excelling also in lasting effect.

Example 5

As a hyacinthine scented formulated composition, a basic aroma composition formed of the components as shown in the following Table 4 was prepared.

TABLE 4

A Hyacinthine Scented, Basic Formulated Aroma Composition

| Blended Component | Blended Amount (g) |
|---|---|
| phenylacetaldehyde | 100 |
| cinnamic alcohol | 150 |
| hyacinth absolute | 20 |
| phenylethyl alcohol | 100 |
| α-ionone | 30 |
| benzyl propionate | 70 |
| ylang-ylang oil | 20 |
| amylcinnamic aldehyde | 50 |
| isoeugenol | 40 |
| benzyl alcohol | 100 |
| dimethylbenzyl carbinol | 30 |
| galbanum resinoid | 50 |
| phenylacetaldehyde dimethyl acetal | 80 |
| lauryl alcohol | 20 |
| nerol | 80 |
| heliotropine | 60 |
| Total | 1000 |

Novel hyacinth-scented formulated aroma compositions were prepared by adding 0.1 g of the 6,8,10-undecatrien-3-ol as prepared in Example 1 or 0.1 g of the 6,8,10-undecatrien-4-ol as prepared in Example 2, to 99.9 g each of the above composition. Aromas of these novel formulated aroma compositions and that of the hyacinth-scented aroma composition as prepared in the above to which neither of the compounds was added, were compared by ten expert panelists. The result of the sensory evaluation is shown in Table 5.

TABLE 5

| Compound Blended | Odor Evaluation |
|---|---|
| none | Control |
| 6,8,10-undecatrien-3-ol | hyacinthine scent with emphasized natural note compared with the control |
| 6,8,10-undecatrien-4-ol | hyacinthine scent with emphasized natural note compared with the control |

As above, all of the ten expert panellists evaluated both of the hyacinthine scented formulated aroma compositions blended with either one of the aroma compounds as well reproducing the characteristic scent of natural hyacinth and markedly excelling also in lasting effect.

Example 6

Odor Evaluation of 6E form and 6Z form of 6,8,10-undecatrien-3-ol

In relation to the 6,8,10-undecatrien-3-ol as obtained in Example 1 in which the ratio of the geometrical isomers at 6-position, E:Z=10:7, odors of (6E,8E)-6,8,10-undecatrien-3-ol and (6Z,8E)-6,8,10-undecatrien-3-ol were evaluated by gas chromatography-olfactometry.

Odor Evaluation (6E,8E)-6,8,10-undecatrien-3-ol: woody green note accompanied by fresh fruity characteristics (6Z,8E)-6,8,10-undecatrien-3-ol: sharp, woody green note accompanied by natural and fresh fruity characteristics Example 7

Odor Evaluation of 6E Form and 6Z Form of 6,8,10-undecatrien-4-ol)

In relation to the 6,8,10-undecatrien-4-ol as obtained in Example 2 in which the ratio of the geometrical isomers at 6-position, E:Z=65:35, odors of (6E,8E)-6,8,10-undecatrien-4-ol and (6Z,8E)-6,8,10-undecatrien-4-ol were evaluated by gas chromatography-olfactometry.

Odor Evaluation (6E,8E)-6,8,10-undecatrien-4-ol: mild green note and sweet fruity note rich in naturality and freshness (6Z,8E)-6,8,10-undecatrien-4-ol: woody green note and sharp, sweet fruity note rich in naturality and freshness.

The invention claimed is:

1. 6,8,10-Undecatrien-3-ol or 6,8,10-undecatrien-4-ol, which are represented by the following formula (1):

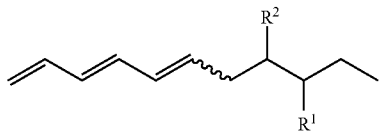

(1)

[in the formula, either one of $R^1$ and $R^2$ stands for hydrogen, and the other stands for hydroxy, the wavy line signifying cis-form, trans-form or a mixture of cis- and trans-forms at an optional ratio].

2. An aroma composition which is characterized by containing 6,8,10-undecatrien-3- or -4-ol of the formula (1) in claim 1 as the active ingredient.

3. A product characterized by containing the aroma composition of claim 2.

4. A method of producing 6,8,10-undecatrien-3-ol which is represented by the following formula (5)

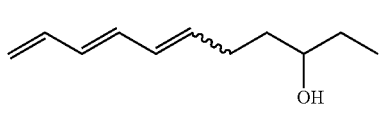

(5)

[in the formula, the wavy line signifies cis-form, trans-form or a mixture of cis- and trans-forms at an optional ratio] which is characterized by subjecting a phosphonium salt represented by the following formula (2)

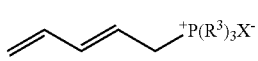

(2)

[in the formula, $R^3$ stands for an aryl and X stands for a halogen]

or a phosphonate of the following formula (3)

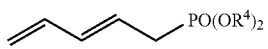
(3)

[in the formula, R⁴ stands for a $C_{1-8}$ alkyl or aryl]
to Wittig reaction or Horner-Emmons reaction, with a lactol of the following formula (4)

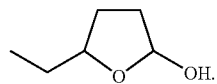
(4)

5. A method for producing 6,8,10-undecatrien-4-ol which is represented by the following formula (7)

(7)

[in the formula, the wavy line signifies cis-form, trans-form, or a mixture of cis- and trans-forms at an optional ratio]

which is characterized by reducing 6,8,10-undecatrien-4-one represented by the following formula (6)

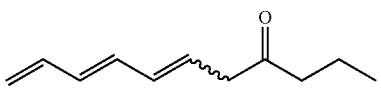
(6)

[in the formula, the wavy line signifies cis-form, trans-form, or a mixture of cis- and trans-forms at an optional ratio].

* * * * *